United States Patent
Cedarbaum

(10) Patent No.: US 7,479,273 B2
(45) Date of Patent: *Jan. 20, 2009

(54) METHOD OF ADMINISTERING AND USING VEGF INHIBITORS FOR THE TREATMENT OF RENAL CELL CANCER

(75) Inventor: Jesse M. Cedarbaum, Larchmont, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/074,096

(22) Filed: Feb. 29, 2008

(65) Prior Publication Data

US 2008/0188419 A1    Aug. 7, 2008

Related U.S. Application Data

(62) Division of application No. 11/149,738, filed on Jun. 10, 2005, now Pat. No. 7,354,580.

(60) Provisional application No. 60/578,499, filed on Jun. 10, 2004.

(51) Int. Cl.
*A61K 38/18* (2006.01)
*C07K 14/71* (2006.01)
*C12N 15/62* (2006.01)

(52) U.S. Cl. ............ 424/134.1; 424/192.1; 514/2; 514/12; 530/350; 536/23.4

(58) Field of Classification Search ............ None
See application file for complete search history.

(56) References Cited

U.S. PATENT DOCUMENTS 6,897,294 B2    5/2005    Davis-Smyth et al.

FOREIGN PATENT DOCUMENTS

| WO | WO 00/75319 | 12/2000 |
| WO | WO 02/060489 | 8/2002 |
| WO | WO 2004/106378 | 12/2004 |
| WO | WO 2004/110490 | 12/2004 |
| WO | WO 2005/000220 | 1/2005 |
| WO | WO 2005/000895 | 1/2005 |

OTHER PUBLICATIONS

Phillips, A.J. (2001). The challenge of gene therapy and DNA delivery. J. Pharm. Pharmacol. 53:1169-1174.*
Palú et al. (1999). In pursuit of new developments for gene therapy. J. Biotechnol. 68:1-13.*
Glade-Bender, J. et al. (2003) Expert Opin. Biol. Ther. 3(2):263-276.
Holash, J. et al. (2002) Proc. Natl. Acad. Sci. USA 99(17):11393-11398.
Huang, J. et al. (2003) Proc. Natl. Acad. Sci. USA 100(13):7785-7790.
Kim, E.S. et al. (2002) Proc. Natl. Acad. Sci. USA 99 (17):11399-11404.
Poon, R. et al. (2001) Journal of Clinical Oncology 19 (4):1207-1225.
Gerber, H-P et al. (2000) Cancer Research 60: 6253-6258.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

A method of treating a human patient suffering from cancer, comprising administering an effective amount of a vascular endothelial growth factor (VEGF) trap antagonist to the human patient, the method comprising: (a) administering to the patient an initial dose of at least approximately 0.3 mg/kg of the VEGF antagonist; and (b) administering to the patient a plurality of subsequent doses of the VEGF antagonist in an amount that is approximately the same or less of the initial dose, wherein the subsequent doses are separated in time from each other by at least one day. The methods of the invention are useful for treating a human cancer selected from the group consisting of renal cell carcinoma, pancreatic carcinoma, breast cancer, prostate cancer, colorectal cancer, malignant mesothelioma, multiple myeloma, ovarian cancer, and melanoma. The invention is further useful for treating a condition which benefits from the reduction of VEGFA and placental growth factor (PLGF).

6 Claims, No Drawings

METHOD OF ADMINISTERING AND USING VEGF INHIBITORS FOR THE TREATMENT OF RENAL CELL CANCER

RELATED APPLICATIONS

This application is a divisional application of U.S. application Ser. No. 11/149,738 filed 10 Jun. 2005, now U.S. Pat. No. 7,354,580 now allowed, which claims the benefit under 35 USC 119(e) to U.S. Ser. No. 60/578,499 filed 10 Jun. 2004, which applications are incorporated by reference in their entirety.

FIELD OF THE INVENTION

The invention relates to methods of promoting regression of tumors and metastases by inhibiting vascular endothelial growth factor (VEGF) activity.

DESCRIPTION OF RELATED ART

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF fusion protein antagonist, termed a "VEGF$_{R1R2}$ trap" or "VEGF trap" antagonist has been described (Kim et al. (2002) Proc. Natl. Acad. Sci. USA 99:11399-404; Holash et al. (2002) Proc. Natl. Acad. Sci. USA 99:11393-8), which applications are specifically incorporated by reference in their entirety.

BRIEF SUMMARY OF THE INVENTION

In a first aspect, the invention features a method of treating a human patient suffering from cancer, comprising administering an effective amount of a vascular endothelial growth factor (VEGF) fusion protein trap antagonist to the human patient, the method comprising: (a) administering to the patient an initial dose of at least approximately 0.3 mg/kg of the VEGF trap antagonist; and (b) administering to the patient a plurality of subsequent doses of the VEGF trap antagonist in an amount that is approximately the same or less of the initial dose, wherein the subsequent doses are separated in time from each other by at least one day. The dosing regimen of the invention allows early attainment of an efficacious target trough serum concentration by providing an initial dose or doses of VEGF trap antagonist followed by subsequent doses of equal or smaller amounts of trap (greater front loading). The efficacious target trough serum concentration is reached in 4 weeks or less, preferably 3 weeks or less, more preferably 2 weeks or less, and most preferably 1 week or less, including 1 day or less. The target serum concentration is thereafter maintained by the administration of maintenance doses of equal or smaller amounts for the remainder of the treatment regimen or until suppression of disease symptoms is achieved.

In specific embodiments, the initial dose of the VEGF fusion protein antagonist is in the range of approximately between 0.3 mg per kg body weight (mg/kg/kg) to 30 mg/kg. In a more specific embodiment, the initial dose is in the range of approximately 0.5 mg/kg to 10 mg/kg. In an even more specific embodiment, the initial dose is in the range of approximately 1 mg/kg to 6 mg/kg. Preferably, the cumulative weekly dose is in the range of 0.3 to 30 mg/kg.

In specific embodiments, at least one subsequent dose of the VEGF fusion protein antagonist is in the range of approximately between 0.3 mg/kg body weight to 30 mg/kg. In a more specific embodiment, at least one subsequent dose is in the range of approximately 0.5 mg/kg to 10 mg/kg. In an even more specific embodiment, at least one; subsequent dose is in the range of approximately 1 mg/kg to 6 mg/kg.

In one embodiment, subsequent doses are separated in time from each other by at least 1 day, at least 1 week, at least 2 weeks, at least 3 weeks, at least 1 month, at least 2 months, or at least 3 months. According to the invention, the cycle of dosing is preferably repeated as necessary to achieve suppression of the disease symptoms.

The method of the invention may be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. More specifically, the human patient treated by the method of the invention is a patient diagnosed with one of the following cancers: renal cell carcinoma, pancreatic carcinoma, breast cancer, prostate cancer, colorectal cancer, malignant mesothelioma, multiple myeloma, ovarian cancer, or melanoma. In a specific embodiment, the cancer being treated is renal cell carcinoma. In another embodiment, the cancer being treated is pancreatic carcinoma. In another embodiment, the cancer being treated is breast cancer. In another embodiment, the cancer being treated is colorectal cancer. In another embodiment, the cancer being treated is malignant mesothelioma. In another embodiment, the cancer being treated is multiple myeloma. In another embodiment, the cancer being treated is ovarian cancer. In another embodiment, the cancer being treated is melanoma. In another embodiment, the cancer being treated is non-small cell lung cancer. In another embodiment, the cancer being treated is prostate cancer.

The VEGF fusion protein trap antagonist is a dimer comprising two fusion proteins each composed of immunoglobulin (Ig)—like domains from two different VEGF receptors fused to a multimerizing component, wherein each fusion protein is capable of forming a higher order complex through interaction of multimerizing components on different fusion proteins. The VEGF trap antagonist useful in the method of the present invention is a dimer capable of binding both vascular endothelial growth factor A (VEGFA) and placental growth factor (PLGF), and is selected from the group consisting of acetylated Flt-1(1-3)-Fc, Flt-1 (1-3$_{R->N}$)-Fc, FLt-1 (1-3$_{AB}$)-Fc, Flt-1(2-3$_{AB}$)-Fc, Flt-1(2-3)-Fc, Flt-1D2-VEGFR3D3-FcΔC1(a), Flt-1D2-Flk-1D3-FcΔC1(a), and VEGFR1R2-FcΔC1(a). In a specific and preferred embodiment, the VEGF trap antagonist is VEGFR1R2-FcΔC1(a) (also termed VEGF trap$_{R1R2}$) having the nucleotide sequence set forth in SEQ ID NO: 1 and the amino acid sequence set forth in SEQ ID NO: 2. The invention encompasses the use of a VEGF trap that is at least 90%, 95%, 98%, or at least 99% homologous with the nucleotide sequence set forth in SEQ ID NO: 1 and/or the amino acid sequence set forth in SEQ ID NO:2.

Administration of the agent may be by any method known in the art, including subcutaneous, intramuscular, intradermal, intraperitoneal, intravenous, intranasal, or oral routes of administration. In a preferred embodiment, the initial dose is administered by subcutaneous injection or intravenous injection. In further embodiments, the subsequent doses are administered by subcutaneous injection. In a preferred embodiment, the initial dose and at least one subsequent dose are administered by subcutaneous injection.

In a second aspect, the invention features a method of treating a human patient susceptible to or diagnosed with a disorder which is inhibited by an agent capable of blocking or inhibiting vascular endothelial growth factor A (VEGF A), wherein the agent capable of blocking or inhibiting VEGFA is a VEGF trap antagonist, the method comprising: (a) administering to the patient an initial dose of at least approximately 0.3 mg/kg of the VEGF trap; and (b) administering to the patient a plurality of subsequent doses of the VEGF trap in an amount that is approximately the same or less of the initial dose, wherein the subsequent doses are separated in time from each other by at least one day. In a specific and preferred embodiment, the VEGF trap antagonist is VEGFR1R2-Fc$\Delta$C1 (a) (also termed VEGF trap$_{R1R2}$) having the nucleotide sequence set forth in SEQ ID NO: 1 and the amino acid sequence set forth in SEQ ID NO: 2.

In a third embodiment, the invention features a therapeutic method of the invention optionally combined with a second chemotherapeutic agent. Chemotherapeutic agents combinable with administration of VEGF trap include, for example, anti-VEGF antibodies, anthracycline derivatives, such as doxorubicin or epirubicin taxol, and taxoid derivatives such as paclitaxel (Taxol®) and related derivatives.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

GENERAL DESCRIPTION

Vascular endothelial growth factor/vascular permeability factor (VEGF) was initially identified as a tumor-derived factor capable of increasing vascular permeability. It was subsequently found to be a proliferative factor for endothelial cells. In the embryo, VEGF is absolutely essential for the development of the vasculature. In the adult, VEGF is up-regulated in a variety of normal and pathological processes associated with increased vascular permeability and angiogenesis.

The family of VEGF-related angiogenic growth factors is comprised of VEGF itself (VEGF-A) and the related proteins VEGF-B, -C, -D and E, and placental growth factor (PLGF). In addition, there are at least four different isoforms of VEGF-A. However, as some members of the family have only recently been identified, their biological importance is still poorly understood. The actions of VEGF and its related factors are mediated by a group of three receptor tyrosine kinases, VEGFR1, VEGFR2 and VEGFR3.

The importance of VEGF in tumor angiogenesis has been demonstrated in a number of animal models, where blocking VEGF signaling by a variety of strategies has proven effective at decreasing angiogenesis and inhibiting tumor growth (Gourley and Williamson (2000) Curr. Pharm. Des. 6:417-39). The permeability-inducing properties of VEGF are also of pathological importance, for example in edema formation, ascites and pleural effusions related to cancer. The degree of vascularization and of VEGF production have been proposed as prognostic factors for many types of solid and hematological malignancies (reviewed by Poon et al (2001) J. Clin. Oncol. 19:1207-1225).

Consistent with predictions from animal studies, blockade of VEGF using a humanized monoclonal antibody has emerged reporting promising results in cancer patients, based on preliminary reports from early clinical trials (Bergsland et al. (2000) ASCO Abstract #939). The VEGF fusion protein trap antagonist, because of its greater affinity for VEGF and its ability to bind other VEGF family members such as the PlGFs, is a potent and useful anti-cancer therapeutic agent.

DEFINITIONS

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding). Efficacy can be measured in conventional ways, depending on the condition to be treated. For cancer therapy, efficacy can, for example, be measured by assessing the time to disease progression (TTP), or determining the response rates (RR). Therapeutically effective amount also refers to a target serum concentration, such as a trough serum concentration, that has been shown to be effective in suppressing disease symptoms when maintained for a period of time.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, prostate cancer, colon cancer, colorectal cancer, endometrial carcinoma, salivary gland carcinoma, kidney cancer, prostate cancer, vulval cancer, thyroid cancer, hepatic carcinoma and various types of head and neck cancer. More specifically, the methods of the invention are useful for treating any condition or disease which is ameliorated or inhibited with a VEGF inhibitor. Accordingly, when the disease or condition is cancer, the cancer treated by the method of the invention is one which is ameliorated or inhibited by administration of a VEGF inhibitor.

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF blocker or inhibitor is a VEGF receptor-based antagonist including, for example, an anti-VEGF antibody, or a VEGF trap antagonist such as VEGFR1R2-FcΔC1(a) (SEQ ID NOs:1-2). For a complete description of VEGF-receptor based antagonists including VEGFR1R2-FcΔC1(a), see PCT publication WO/00/75319, the contents of which is herein incorporated by reference in its entirety.

The term "package insert" is used to refer to instructions customarily included in commercial packages of therapeutic products, that contain information about the indications, usage, dosage, administration, contraindications and/or warnings concerning the use of such therapeutic products.

The term "serum concentration," "serum drug concentration," or "serum VEGF trap concentration" refers to the concentration of a drug, such as the VEGF fusion protein trap antagonist, in the blood serum or plasma of an animal or human patient being treated with the drug. Serum concentration is preferably determined by immunoassay. Preferably, the immunoassay is an ELISA according to the procedure disclosed herein.

The term "peak serum concentration" refers to the maximal serum drug concentration shortly after delivery of the drug into the animal or human patient, after the drug has been distributed throughout the blood system, but before significant tissue distribution, metabolism or excretion of drug by the body has occurred.

The term "trough serum concentration" refers to the serum drug concentration at a time after delivery of a previous dose and immediately prior to delivery of the next subsequent dose of drug in a series of doses. Generally, the trough serum concentration is a minimum sustained efficacious drug concentration in the series of drug administrations. Also, the trough serum concentration is frequently targeted as a minimum serum concentration for efficacy because it represents the serum concentration at which another dose of drug is to be administered as part of the treatment regimen. If the delivery of drug is by intravenous administration, the trough serum concentration is most preferably attained within 1 day of a front loading initial drug delivery. If the delivery of drug is by subcutaneous administration, the peak serum concentration is preferably attained in 3 days or less. According to the invention, the trough serum concentration is preferably attained in 4 weeks or less, preferably 3 weeks or less, more preferably 2 weeks or less, most preferably in 1 week or less, including 1 day or less using any of the drug delivery methods disclosed herein.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "front loading" when referring to drug administration is meant to describe an initially higher dose followed by the same or lower doses at intervals. The initial higher dose or doses are meant to more rapidly increase the animal or human patient's serum drug concentration to an efficacious target serum concentration. According to the present invention, front loading is achieved by an initial dose or doses delivered over three weeks or less that causes the animal's or patient's serum concentration to reach a target serum trough concentration. Preferably, the initial front loading dose or series of doses is administered in two weeks or less, more preferably in 1 week or less, including 1 day or less. Most preferably, where the initial dose is a single dose and is not followed by a subsequent maintenance dose for at least 1 week, the initial dose is administered in 1 day or less. Where the initial dose is a series of doses, each dose is separated by at least 3 hours, but not more than 3 weeks or less, preferably 2 weeks or less, more preferably 1 week or less, most preferably 1 day or less.

The VEGF Fusion Protein Trap Antagonist

In a preferred embodiment, the VEGF trap is a receptor-Fc fusion protein consisting of the principal ligand-binding portions of the human VEGFR1 and VEGFR2 receptor extracellular domains fused to the Fc portion of human IgG1. Specifically, the VEGF Trap consists essentially of Ig domain 2 from VEGFR1, which is fused to Ig domain 3 from VEGFR2, which in turn is fused to the Fc domain of IgG1 (SEQ ID NO:2).

In a preferred embodiment, an expression plasmid encoding the VEGF trap is transfected into CHO cells, which secrete VEGF trap into the culture medium. The resulting VEGF trap is a dimeric glycoprotein with a protein molecular weight of 97 kDa and contains ~15% glycosylation to give a total molecular weight of 115 kDa.

Since the VEGF trap binds its ligands using the binding domains of high-affinity receptors, it has a greater affinity for VEGF than do monoclonal antibodies. The VEGF trap binds VEGF-A ($K_D$=0.5 μM), PLGF1 ($K_D$=1.3 nM), and PLGF2 ($K_D$=50 pM); binding to other VEGF family members has not yet been fully characterized.

Treatment Population

The method of the invention may be used to treat tumors arising in the brain and meninges, oral pharynx, lung and bronchial tree, gastrointestinal tract, male and female reproductive tract, muscle, bone, skin, connective tissue, immune system, blood forming cells and bone marrow, liver and urinary tract, and special sensory organs such as the eye. More specifically, human patients suffering from renal cell carcinoma, pancreatic carcinoma, breast cancer, prostate cancer, colorectal cancer, malignant mesothelioma, multiple myeloma, ovarian cancer, or melanoma may be treated with the VEGF trap as described below.

Combination Therapies

In numerous embodiments, a VEGF fusion protein trap antagonist may be administered in combination with one or more additional compounds or therapies, including a second VEGF trap molecule. Combination therapy includes administration of a single pharmaceutical dosage formulation which contains a VEGF trap and one or more additional agents; as well as administration of a VEGF trap and one or more additional agent(s) in its own separate pharmaceutical dosage formulation. For example, a VEGF trap and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycins, puromycin, quelamycin, rodorubicin, streptonnigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TOXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts; acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Pharmacokinetics and Safety of the VEGF Fusion Protein Trap Antagonist in Primates Preclinical toxicology studies were conducted with the VEGF trap (SEQ ID NO:2) in primates and rodents. Four- and thirteen week toxicology studies in cynomolgus monkeys showed that the VEGF trap was well tolerated when administered subcutaneously three times per week at doses of 1.5, 5, and 15 mg/kg (four week study), or twice a week at 1.5, 5, 15 or 30 mg/kg in the thirteen-week study. The VEGF trap was not highly immunogenic after four weeks in monkeys; only one mid-dose animal developed low titer antibodies.

Example 2

Treatment of Solid Tumors or Non-Hodgkin's Lymphoma

Patients with refractory solid tumors or non-Hodgkin's lymphoma receiving no concurrent treatment for their cancer are treated with the VEGF trap as follows. The dose levels range from 0.3 mg/kg to 30 mg/kg given subcutaneously. Each patient receives a single initial dose of the VEGF trap followed by four weeks of observation and pharmacokinetic blood sampling. Beginning in the fifth week of the study, patients receive a series of 6 weekly injections at the assigned dose level. Plasma levels of the VEGF trap, and VEGF, both free and bound together as a complex, are monitored. Tumor burden is assessed at the beginning and end of the weekly dosing period and periodically during treatment; patients with stable disease, partial or complete responses may continue dosing for up to an additional 6 months in a continuation study. At higher dose levels where efficacy might be anticipated, patients undergo Dynamic Contrast Enhanced MRI scans to assess effects of VEGF trap administration on tumor perfusion.

We claim:

1. A method of treating a human patient suffering from renal cell cancer, comprising administering an effective amount of a fusion protein vascular endothelial growth factor (VEGF) antagonist VEGFR1R2-FcΔC1(a) (SEQ ID NO:2) to the human patient, the method comprising:
   (a) administering to the patient an initial dose of at least approximately 0.5 to 10 mg/kg of the VEGF antagonist; and
   (b) administering to the patient a plurality of subsequent doses of the VEGF antagonist in an amount that is approximately the same or less of the initial dose, wherein the subsequent doses are separated in time from each other by at least one day.

2. The method of claim 1, wherein the initial dose is selected from the group consisting of approximately 1 mg/kg, 2 mg/kg, 3 mg/kg, 4 mg/kg, 5 mg/kg and 6 mg/kg.

3. The method of claim 1, wherein subsequent doses are separated in time from each other by at least two weeks.

4. The method of claim 1, wherein administration is intravenous.

5. The method of claim 1, further comprising administering a second therapeutic agent.

6. The method of claim 5, wherein the second therapeutic agent is a cytotoxic agent, a chemotherapeutic agent or a growth inhibitory agent.

* * * * *

SEQUENCE LISTING

<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaaacttgt aaaccgagac     540
ctaaaaaccc agtctgggag tgagatgaag aaattttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
```

```
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga     1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
             35                 40                  45

Gly Arg Glu Leu Val Ile Pro Cys Arg Val Thr Ser Pro Asn Ile Thr
         50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
```

-continued

```
                    290                     295                     300
Glu Gln Tyr Asn Ser Thr Tyr Arg Val Val Ser Val Leu Thr Val Leu
305                     310                     315                     320

His Gln Asp Trp Leu Asn Gly Lys Glu Tyr Lys Cys Lys Val Ser Asn
                325                     330                     335

Lys Ala Leu Pro Ala Pro Ile Glu Lys Thr Ile Ser Lys Ala Lys Gly
                340                     345                     350

Gln Pro Arg Glu Pro Gln Val Tyr Thr Leu Pro Pro Ser Arg Asp Glu
                355                     360                     365

Leu Thr Lys Asn Gln Val Ser Leu Thr Cys Leu Val Lys Gly Phe Tyr
                370                     375                     380

Pro Ser Asp Ile Ala Val Glu Trp Glu Ser Asn Gly Gln Pro Glu Asn
385                     390                     395                     400

Asn Tyr Lys Thr Thr Pro Pro Val Leu Asp Ser Asp Gly Ser Phe Phe
                405                     410                     415

Leu Tyr Ser Lys Leu Thr Val Asp Lys Ser Arg Trp Gln Gln Gly Asn
                420                     425                     430

Val Phe Ser Cys Ser Val Met His Glu Ala Leu His Asn His Tyr Thr
                435                     440                     445

Gln Lys Ser Leu Ser Leu Ser Pro Gly Lys
    450                     455
```